(12) United States Patent
Liu et al.

(10) Patent No.: US 7,767,444 B2
(45) Date of Patent: Aug. 3, 2010

(54) CELL ANALYSIS USING LASER WITH EXTERNAL CAVITY

(75) Inventors: Ai Qun Liu, Singapore (SG); Xiao Jun Liang, Singapore (SG); Xu Ming Zhang, Singapore (SG); Yi Sun, Singapore (SG)

(73) Assignee: Nanyang Technological University, Singapore (SG)

( * ) Notice: Subject to any disclaimer, the term of this patent is extended or adjusted under 35 U.S.C. 154(b) by 1429 days.

(21) Appl. No.: 11/139,610

(22) Filed: May 31, 2005

(65) Prior Publication Data
US 2006/0268260 A1    Nov. 30, 2006

(51) Int. Cl.
C12M 1/34 (2006.01)
C12M 3/00 (2006.01)
G01N 21/00 (2006.01)

(52) U.S. Cl. .............. 435/288.7; 435/288.3; 435/288.5; 435/808; 356/36; 356/72; 356/506; 356/519

(58) Field of Classification Search .............. 435/288.7, 435/808, 288.3, 288.5; 356/72, 36, 519, 356/506
See application file for complete search history.

(56) References Cited

U.S. PATENT DOCUMENTS

| 5,073,024 A | * | 12/1991 | Valette et al. ............... 356/481 |
| 5,608,519 A | | 3/1997 | Gourley et al. |
| 5,793,485 A | | 8/1998 | Gourley |
| 5,808,743 A | * | 9/1998 | Stephens et al. ............ 356/614 |
| 5,933,233 A | * | 8/1999 | Gunther ...................... 356/318 |
| 7,142,738 B2 | * | 11/2006 | Lee .............................. 385/14 |
| 2002/0197603 A1 | * | 12/2002 | Chow et al. .................... 435/6 |
| 2005/0068536 A1 | * | 3/2005 | Schwabe ..................... 356/436 |
| 2005/0105567 A1 | * | 5/2005 | Sacher ......................... 372/20 |
| 2009/0251682 A1 | * | 10/2009 | Wang et al. ................... 356/36 |

OTHER PUBLICATIONS

Valcarcel et al., "We Need Reliable Ways To Bypass Preliminary Operations In (Bio)Chemical Measurement" *Trends in Analytical Chemistry*, vol. 21, No. 4, p. 211-212 (2002).
Katsuragi et al., "Screening for Microorganisms with Specific Characteristics by Flow Cytometry and Single-Cell Sorting" *Journal of Bioscience and Bioengineering*, vol. 89, No. 3, 217-222 (2000).

(Continued)

Primary Examiner—William H Beisner
Assistant Examiner—Nathan A Bowers
(74) Attorney, Agent, or Firm—Birch, Stewart, Kolasch & Birch, LLP

(57) ABSTRACT

An apparatus and method for analyzing biological cells and other particles using an external laser cavity. Microfluidic channels contain and transport biological cells to be analyzed. A laser diode provides light for cell analysis. An external cavity is provided between one surface of the laser diode and a mirror opposite thereto. A microlens set focuses the light on only one cell as it passes through the external cavity. The presence of the cell in the external cavity gives a weak feedback toward the laser diode. The emission frequency and the output power of the laser are both functions of the length of the external cavity. Therefore, the variation of cavity length can be deduced from these parameters, where the variation is caused by changing the refractive index or size of the cell in the cavity.

30 Claims, 6 Drawing Sheets

OTHER PUBLICATIONS

Sorensen et al., "Absolute Refractive Index Determination by Microinterferometric Backscatter Detection" *Analytical Chemistry*, vol. 75, No. 8, pp. 1946-1953 (2003).

Lunazzi et al., "Fabry-Perot Laser Interferometry to Measure Refractive Index or Thickness of Transparent Materials" *Journal of Physics E: Scientific Instrucments*, vol. 6, pp. 237-240 (1973).

Tchoukalova et al., "A Quick, Reliable, and Automated Method for Fat Cell Sizing" *Journal of Lipid Research*, vol. 44, pp. 1795-1801 (2003).

Sun et al., "A High-Accuracy Cell Sorter Using Electroosmotically-Driven Microfluidic System" *Proceeding of Asia-Pacific Conference of Transducers and Micro-Nano Technology*, pp. 267-271 (2004).

Liang et al., "An Approach to Cancer Cell Diagnosis Using Integrated Photonic Chip" *Proceeding of Asia-Pacific Conference of Transducers and Micro-Nano Technology*, pp. 276-280 (2004).

McDonald et al., "Poly(dimethylsiloxane) as a Material for Fabricating Microfluidic Devices" *Accounts of Chemical Research*, vol. 35, No. 7, pp. 491-499 (2002).

Petermann, *Laser Diode Modulation and Noise*, Ch. 9, pp. 251-261 (1998).

Liu et al., "Micromachined Wavelength Tunable Laser With an Extended Feedback Model" *IEEE Journal on Selected Topics in Quantum Electronics*, vol. 8, No. 1, pp. 73-79 (2002).

Zhang et al., "Discrete Wavelength Tunable Laser Using Microelectromechanical Systems Technology" *Applied PHysics Letters*, vol. 84, No. 3, pp. 329-331 (2004).

Liu et al., "Tunable Laser Using Micromachined Grating with Continuous Wavelength Tuning" *Applied Physics Letters*, vol. 85, No. 17, pp. 3684-3686 (2004).

Mishchenko et al., "Effective Medium Approximations for Heterogeneous Particles" *Light Scattering by Nonspherical Particles* Ch. 9, pp. 271-283 (2000).

Bereiter-Hahn et al., "Quantitative Reflection Contrast Microscopy of Living Cells" *Journal of Cell Biology*, vol. 82, pp. 767-779 (1979).

Backman et al., "Detection of Preinvasive Cancer Cells" Nature, 406, pp. 35-36 (2000).

Chen et al., "Propagation Loss Reduction of Photonic Crystal Slab Waveguides by Microspheres" *Optics Express*, vol. 12, No. 17, pp. 3934-3939 (2004).

Nakai et al., "Remarkably Size-Regulated Cell Invasion by Artificial Viruses. Saccharide-Dependent Self-Aggregation of Glycoviruses and Its Consequences in Glycoviral Gene Delivery" *J. Am. Chem. Soc.*, 125, pp. 8465-8475 (2003).

Ehrlicher et al., "Guiding Neuronal Growth with Light" *Proc. Nat. Aca. Sci.* vol. 99, No. 25, pp. 16024-16028 (2002).

Lee et al., "Styrylpyrone Derivative (SPD) Induces Apoptosis in a Caspase-7-Dependent Manner in the Human Breast Cancer Cell Line MCF-7" *Cancer Cell International*, 3:16, pp. 1-8 (2003).

* cited by examiner

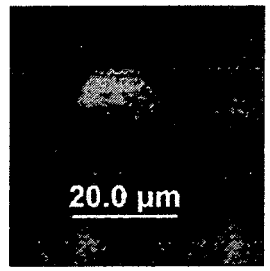 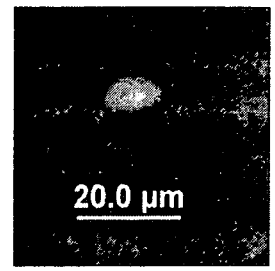
Fig. 6a　　　　　　　　　　　　Fig. 6b
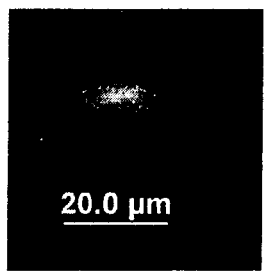 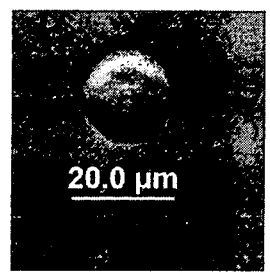 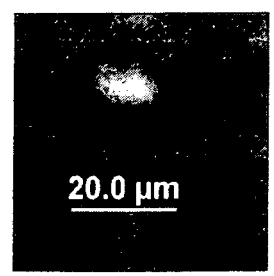
Fig. 6c　　　　　　Fig. 6d　　　　　　Fig. 6e

US 7,767,444 B2

CELL ANALYSIS USING LASER WITH EXTERNAL CAVITY

BACKGROUND OF THE INVENTION

1. Field of the Invention

This present invention relates to the analysis and processing of biological cells and other particles and more particularly to a method and device for analyzing and processing biological cells using a laser diode with an external cavity.

2. Discussion of the Background

In recent years, rapid in-situ monitoring of biological cells and detection of ultra-small-volume samples, and even of single cells, are in great demand (1). Those analyses and processing may include the determination of morphologic characteristics of cells and biophysical properties of cells, which is of especial importance in the fields of cytochemistry, molecular biology, genetics, immunology, and biomedicine and so forth. Two major fields are environmental monitoring and point-of-care (POC) disease diagnosis including a range of applications, from drinking water quality and food pollution to epidemics and bioterrorism.

Several techniques have been used for cell analysis. One method for analyzing biological cells at high speed is flow cytometry (FCM) (2), wherein the cell samples are marked with fluorescence labels so that they can be recognized in a detection area. The samples are prepared as a cell suspension in a buffer fluid and chemically treated with one or more labels, then they are pumped through a flow channel while being kept in the center of the channel under hydrodynamic focusing control. In the detection area, the cells are illuminated by a focused laser beam and emit fluorescent light. Several detectors are placed at different angles to collect the absorption, scattering or fluorescent light. After finishing the analysis, the cells are separated into different collectors.

The traditional method for determining the refractive index of the cell is interferometry based on flow cytometry (FCM) technology (3,4). The cells to be detected are transported into the sensor zone by the hydrodynamic control and irradiated by a laser light. The laser light is reflected from different regions in the channel, which generate an interference pattern that moves when the refractive index of the flow in the channel changes. Since the cell generally has a refractive index which is different from that of the surrounding medium, the refractive index of the cell is able to be determined by the intensity variations in the interference pattern.

Unfortunately, all these techniques have their individual shortcomings. First, the cell sample requires time-consuming chemical treatment and fluorescence labeling; the fluorescence labels will change the characteristics of the natural cells; moreover, those cells labeled with fluorescent markers cannot be further used, such as for transplantation. Second, the errors of detecting scattered light from an individual cell are quite large; that is why the result from FCM is a statistic distribution and the tested sample requires certain enrichment (concentration of cells), which implies that FCM is not suitable for determining the properties of a single cell. Third, due to the low efficiency of scattering and fluorescence from the small size of biological cells (typically less than 20 µm in diameter) and also a limited area where the fluorescence labels are excited, the signal (intensity) for each cell passing through the detection area may be weak compared to the intensity of incident laser light. Therefore, the limits of sensitivity of FCM depend critically on the power of the incident laser beam and magnitude of the perturbations in the scattered or fluorescent light caused by different variants of the biological cells. Finally, a flow cytometer is a big and expensive machine; it costs normally from $200,000 to $500,000 and needs a trained operator.

Recently, Gourley (U.S. Pat. No. 5,608,519) used a vertical cavity surface emitting laser (VCSEL) as a sensor to analyze red blood cells. By placing the cells within the resonant cavity as one part of the gain medium, some parameters of the cells can be obtained by analyzing the laser beam emitted from the VCSEL. For example, the emission spectrum of VCSEL includes information on the cell ingredient because of the specific energy level structure. The cell size can be analyzed by the distribution of transversal modes. However, this method has its shortcomings. First, the fabrication for this peculiar VCSEL is very complicated and vulnerable. Making a channel within the laser die increases the difficulty of the process. Second, the dimension of the channel is limited by the size of VCSEL. Moreover, this apparatus can only analyze cells with a narrow size range under a certain channel width. Thus, big cells may be distorted in the channel and small cells might not be efficient enough in influencing the laser emission. Third, the cells to be analyzed can not be exactly located in the middle of channel without microflow control. Finally, it is very difficult to make the VCSEL resonant. Since the biological cell serves as a part of the gain medium, whether the laser will produce an emission after passing through the cells many times will be determined by the energy level structures of the cells. If the cells have a very strong absorption, the laser will not lase because of the high loss, and the cavity can not operate in resonance.

Accordingly, while prior art devices allow for analyzing cells, it is desirable to improve these devices by having systems which are more accurate, work with a single operation, have low costs, and high accuracy.

BRIEF DESCRIPTION OF DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings:

FIGS. 6a, 6b, 6c, 6d and 6e shows the microscopy images of five cancerous cells.

DETAILED DESCRIPTION OF THE INVENTION

Figure 1:
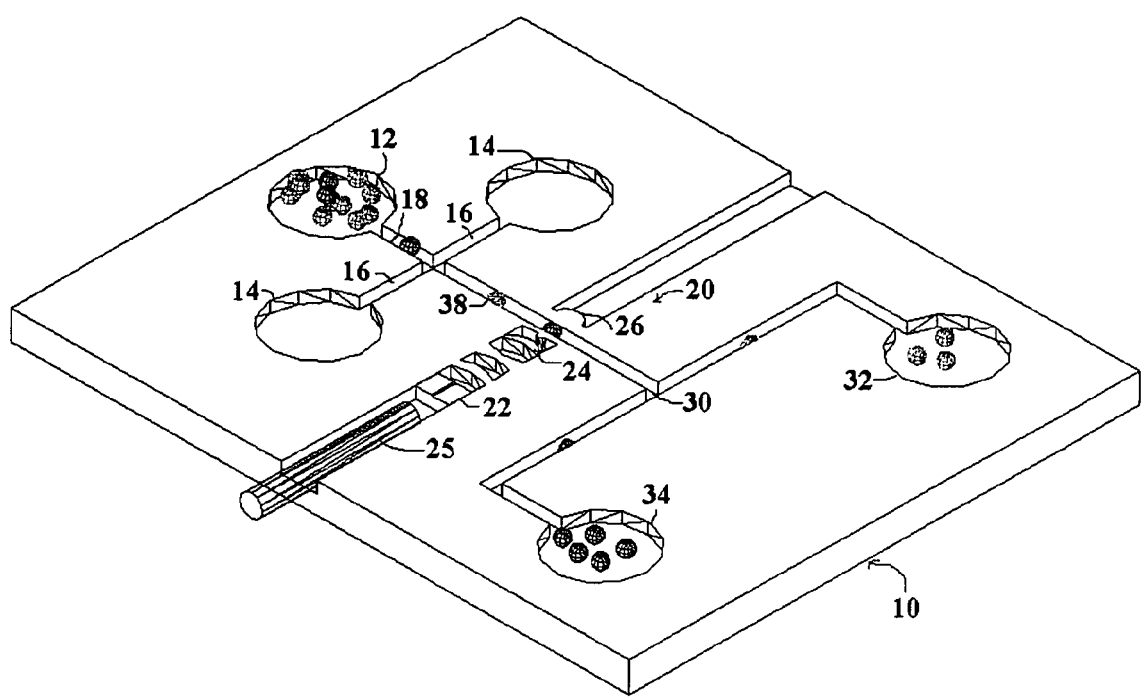
FIG. 1 is a perspective view of a laser apparatus for microscopic and spectroscopic analysis and processing of biological cells according to the present invention.

The present invention seeks to overcome the problems of the prior art by providing a system for biomedical analysis with a single operation, low costs, and high accuracy. The embodiments of the invention may independently provide one or more of the advantages set forth below.

One advantage of the present invention is that the biological cells are able to be non-invasively analyzed without any chemical treatment or fluorescent labeling, which keeps the cells intact and also enables the collected cells to be further used or processed after measurement, especially for therapeutic purposes.

Another advantage of the present invention is that the living cells are measured one by one in the analysis region in real time with high accuracy, which provides an approach for single-molecule detection (SMD) and reduces the sample consumption as well.

A further advantage of the present invention is that the living cells are located within an external laser cavity and analyzed as a weak feedback apparatus. The light that is reflected back from the external cavity after passing through the biological cells once will finally influence the characteristics of laser emission. Therefore, the emission light from the combination laser includes the information about the cells. Furthermore, this analysis system has a very high resolution because of the high sensitivity and multi-amplification function of a laser cavity. The minimum detectable variation in cavity length is theoretically down to 10 nm.

Still another advantage of the present invention is that the analysis system is able to scan the cells while they are moving through the checking point little by little, hence, the biophysical properties of the whole cells may be regenerated according to the detection results.

Yet another advantage of the present invention is that this integrated microchip can be constructed by a PDMS replica fabricated by soft lithography and sealed against a standard glass slide. The employment of cost-efficient material reduces the expense. Meanwhile, the soft lithography provides a rapid molding technique for microchip fabrication, too.

Another advantage of the present invention is the analysis results can be automatically calculated and displayed on a screen. After that a corresponding signal will be sent to a control apparatus to steer the direction of cell flow. The whole chip has a small size enabling portable use.

A further advantage of the present invention is that the channel is suitable for analyzing and controlling the flow of cells of any size under microfluidic control. The flow is driven and steered by the electroosmotic force (EOF) generated by the electrical field applied on the wells. By adjusting the ratio of voltages applied to the electrodes of the sample well and focusing wells, the width of cell flow can be narrowed down to single cell size under the hydrofocusing effects (7), in addition, the samples will always be kept in the center of channel and lined up for detection one by one.

Accordingly, the invention provides microfabricated compact devices and methods for the rapid analysis of biological cells. The cells may be analyzed as living cells. Cell components, such as organelles, or protein complexes, proteins, chromosomes or other particles may also be analyzed. The cells or cell components or other particles are located within an external laser cavity and analyzed in real time as a component of a laser medium.

One object of the present invention is to provide an apparatus for analyzing and determining the biophysical properties of living cells such as size, shape, protein concentration, refractive index and so forth. During the measurement, the cells can be fixed in the analysis region or flow through the external cavity. All data are obtained from the characteristics of the laser emission such as spectrum, power and more. This is because the light reflected by the external cavity disturbs the lasing of the laser diode after passing through the cell interior. Accordingly, the cell properties influence the emission of the laser to a certain extent.

A further object of present invention is to provide a versatile apparatus for analyzing biological cells. For example, cells with different sizes from 1 mm to 100 nm are able to be analyzed in the system because of the tunability of the laser cavity. By adjusting the voltage to obtain a single cell flow, the system can be applied to almost any kind of cells. For analyzing the cells with same size and different content, a mirror will be fixed in a certain position to achieve the optimization sensitivity.

Still another object of the present invention is to provide an apparatus for manipulating cell flow, wherein the electrokinetic force generated by an electric field applied on the reservoirs controls the direction of cell flow, and the width of the flow is narrowed down to single cell scale after hydrodynamic focusing so that the cells are separated and lined up while moving to the analysis region. According to the measurement results, a corresponding control signal is generated to classify the cells into different collection reservoirs. Such an apparatus is further described in a PCT application entitled "Micro-Fluidic Cell Sorter System" which is based on U.S. Provisional Application 60/568,266, filed on May 6, 2004, which is hereby incorporated by reference.

Yet another object of present invention is to provide an apparatus for analyzing biological cells with high sensitivity and resolution, wherein a microlens set is designed to improve the beam quality in size and shape so that only one cell is evenly irradiated by the laser. This strongly increases the efficiency of the irradiation. In addition, even though the weak feedbacks from the cells are non-resonant in the external cavity, they are repeatedly amplified inside the resonant cavity of the laser diode. This will highly improve the sensitivity of cell analysis and remove the requirement for resonance in the external cavity.

Another object of the present invention is to provide an apparatus for analyzing and imaging biological activity in living cells including cell cycle, cell division, chromosome mutation, protein condensation and more, wherein the laser emission is varied as to individual biological activities, thus the information about biological activities is encoded in the emission of the laser. For example, the refractive indices of cancerous cells vary with the protein concentration inside the cells. By monitoring the values of refractive index, the stage of cancer disease could be judged. Another example, the refractive index also indicates the stages of cell cycle. The eukaryotic cells in the S stage have a higher refractive index because of the chromosomes' duplication. However, the G stage has no change in chromosome number.

An additional object of the present invention is to provide an apparatus for analyzing and processing biological cells, which is cost-efficient and disposable. The use of cheap polymer and glass materials has brought the cost down to several dollars per piece. Compared with the traditional cell analysis with FCM or interferometer, this chip is portable, cheap and has easy operation, which may pave the way for the application of point of care diagnostics or clinical diagnosis at home.

Different embodiments of the invention may individually accomplish only one, or less than all of the above stated objects of the invention.

The present invention may be applied to the diagnosis of diseases that are relevant to certain specific properties of the cells. As an example, cancer diseases are able to be diagnosed by this method. It has been well known that cancer as a genetic disease is the result of cumulative alterations in DNA. Most of conventional methods like pap smear, microscopy, and blood testing require time-consuming sample preparation and treatments. Worse, those techniques often discover the diseases after noticing symptoms like a lump or unusual bleeding or discharge. This is because early cancer may not have any symptoms. Detecting cancer early can influence the outcome of the disease. Recent evidence shows that the number of chromosomes inside cells is a critical mark early in the development of cancer, and abnormal numbers of chromosomes in a cell may be the first milestone on the road to cancer. From a biophysics point of view, some physical parameters of living cells such as refractive index (RI) will increase with the increment of chromosome amount, which makes it feasible to diagnose cancers by monitoring cellular biophysical properties.

All cell components can be considered as a protein solution, and the effective refractive index of the cell can be expressed as:

$$n=n_0+\alpha C$$

where $n_0$ is the index of the solvent, $\alpha$ is the specific refraction increment, and C is the concentration of the solute. For protein, $\alpha=0.0018$, it plays a vital role in determining the refractive index of the cell (8).

To achieve the foregoing and other objects, and in accordance with the purposes of the present invention as described herein, a laser system for microscopic and spectroscopic analysis and processing of biological cells is provided. The system includes a semiconductor laser diode and an external cavity comprising a microlens set, and mirror placed opposite thereto, wherein the external cavity serves as a feedback apparatus to influence the emission from the laser. The cell travels through the external cavity and affects the feedback so as to influence the emission from the laser. Because the composition of the cell is different from the surrounding, the emission frequency and output power will be changed as the cell passes by the analysis region. The properties of a living cell can be observed by monitoring the frequency shift and power modulation.

The terms used in this specification have their ordinary meanings in the art. However, to better understand the invention, it is helpful to clarify the meaning of certain terms.

The term "cell" includes both prokaryotic and eukaryotic cells. Cells may be considered as including their various components. Subcellular components, such as organelles or protein complexes may be analyzed in a manner similar to cells. Particles other than cells may also be analyzed in a fashion similar to actual cells.

The term "microfluidic channel" refers to all the channels for containing and flowing the cells and buffer, including but not limited to main channels, focusing channels, and branch channels. The microfluidic channels typically have a diameter of cross-section of from 50 to 100 microns.

The term "cell analysis" refers to the measurement of biophysical properties of the cell, for example, refractive index, cell size, cell shape, or protein concentration.

The term "electrical circuit" refers to the necessary components for applying an electrical field to control a flow direction and/or a flow velocity in the apparatus of the invention. It may include, but is not limited to electrodes, wires, one or more power supplies, one or more controller etc. The electrodes and wires are made of metals like gold, copper or aluminum and are coated on the surface of the substrate or may be embedded in the matrix of the replica. Both the electrodes on the chip and the power supplies may be connected to a printed circuit board, which generates different voltages for flow control. For example, the voltage applied to a focusing well normally is higher than the voltage applied on the inlet wells so that the sample passing through the focusing area will be squeezed into a single cell flow. Meanwhile, a switch on the board will change the polarity on the outlet wells, so the flow direction is subsequently switched.

In some embodiments, electrodes are coated on the substrate beneath the main channel of the microfluidic structure and on the side opposite the microfluidic structure to generate electrical fields, so that electromagnetic force will be strongly enhanced.

Cell Analyzer Architecture and Methods of Cell Analysis

Referring to FIG. 1, there is shown a top view of a laser apparatus for microscopic and spectroscopic analysis and processing of biological cells according to the present invention. In certain embodiments, the system is able to be fabricated by soft photolithography or microcontact printing (μCP) (9). A master is made of a layer of hard material (such as SU-8 photoresist from Microchem Corp. and Sotec Microsystems formulated in gamma butyrolactone (GBL) solvent, Poly(methyl methacrylate) (PMMA) or silicon itself) with a desired thickness by traditional photolithography. After that, a liquid polymer, which may be cured, such as PDMS, Mylar and so on, will be poured on the master, forming a replica after curing (for the instance of PDMS, for example, cured with the ratio of 10:1 and baked for 1 hour at 70 ° C.). Finally, the replica is peeled from the master and bonded to a hard substrate using an inductively coupled plasma (ICP) machine, where both of replica and the substrate are exposed to oxygen plasma for 18-30 seconds and quickly bonded together within 1-2 minutes (8-10).

The apparatus 10 includes an inlet well 12 and two focusing wells 14. Outlet wells 32 and 34 are also provided. A microchannel 18 carries cells to a focusing region where channel 16 meets the cell microchannel 18. Microchannel 38 extends from the focusing region and carries the cells into analysis unit 20. This unit contains optical elements including a diode laser light source 22, a microlens arrangement 24, and mirror 26. The cells recognized in the analysis unit are then sorted in sorting region 30 into channels leading to wells 32 and 34.

The microlens set is designed to focus the beam from the diode on single cells at the laser wavelength and couple the reflection from the mirror into the diode to interfere with the emission of the diode. The microlens focuses the beam down to single cell size so that the cells can be analyzed one by one without overlap. This reduces the beam divergence and energy loss on account of scattering. It also improves the feedback efficiency from the external cavity.

FIG. 2 shows the optical elements of the analysis unit 20 and their relationship to the microchannel 38. These elements are formed on a substrate which is a hard material such as a glass slide, a silicon wafer, or a polymer slab. A laser diode 22 has a typical dimension of 215 μm by 300 μm by 100 μm (but can range from hundreds of microns to millimeter scale) and is assembled on the chip under a microscope to serve as a light source before the bonding process. The laser diode is assembled on the substrate before the replica is bonded to the substrate. A corresponding space in the replica is provided to fit over the laser diode and fiber. This is accomplished by designing the master to prevent the polymer material of the replica from occupying that space. The laser diode has either a natural cut surface with a reflectance of about 30% or has one surface which has an anti-reflective coating with a reflectance of about 0.1%.

Figure 2A:
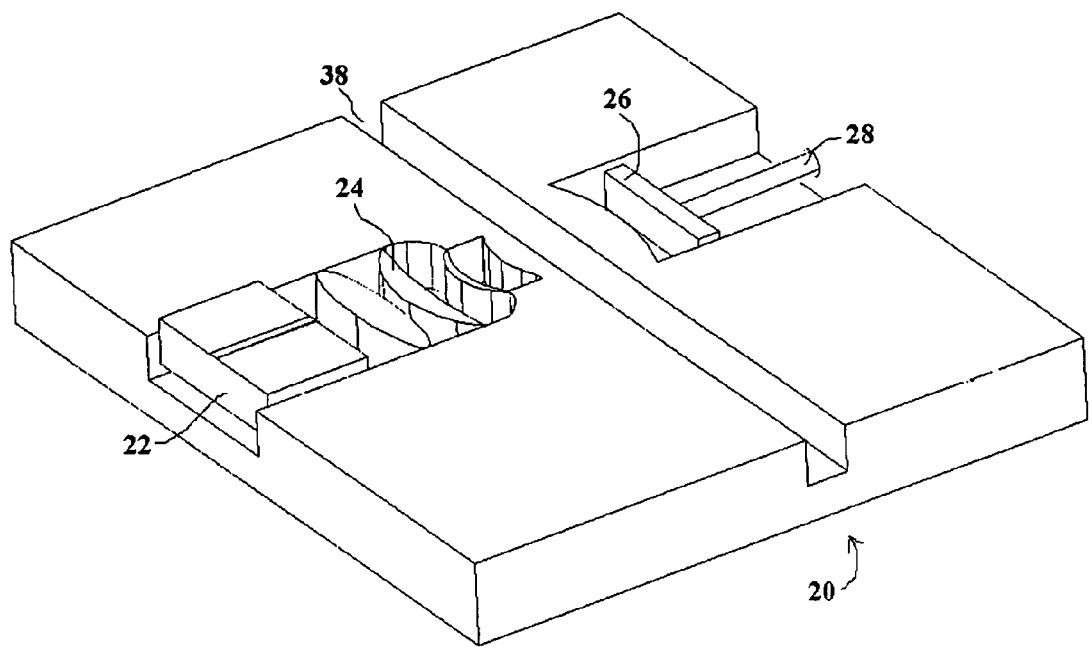
FIG. 2a is a perspective view of a first design of the analysis region for analyzing and processing of biological cells.
Figure 2B:
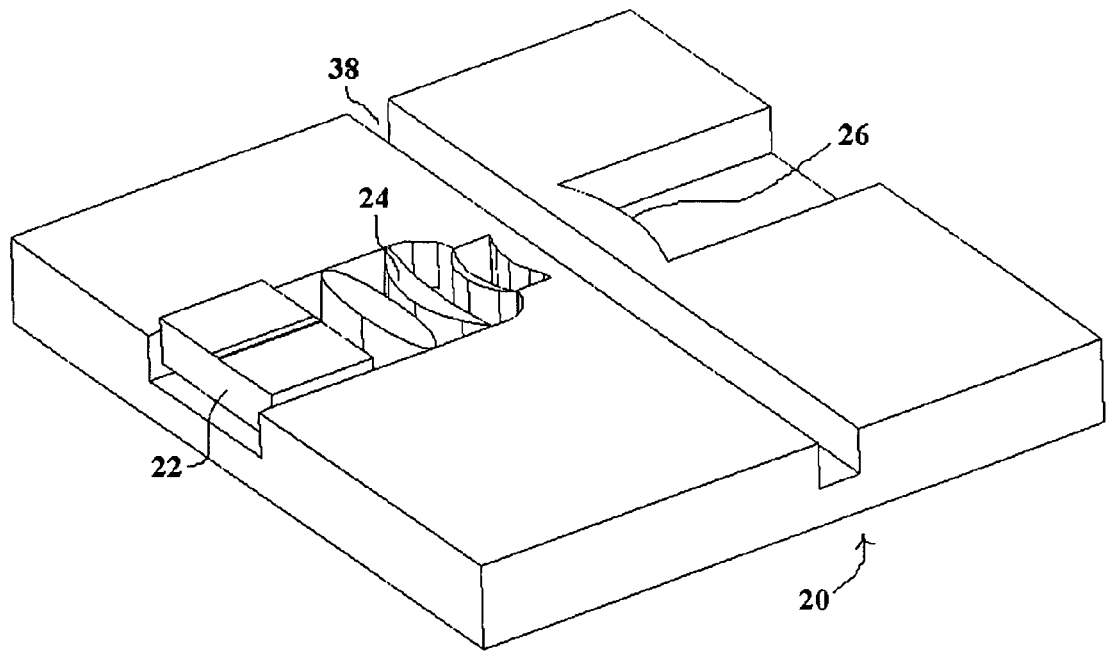
FIG. 2b is a perspective view of a second design of the analysis region.

A mirror, which is preferably plated with gold or other high reflection metal like aluminum, is positioned opposite the diode so as to form an external cavity with one surface of the diode. The mirror can be plane, concave or other shape depending on the applications. A plane mirror forms a Fabry-Perot cavity. A curved mirror forms a plane-convex or plane-concave cavity. The mirror may also be a metal coated aperture face of an optical fiber. A microlens array is set in the external cavity to focus the laser down to single cell size. In some embodiments, the microlens array is cast in the replica matrix (9). In others, the microlens array may be assembled on the substrate and the replica placed over it. An actuator 28 is shown in FIG. 2a for moving the mirror so that the cavity can be tuned. The actuator is operated by a comb driver (13). In FIG. 2b, the mirror 26 is fixed rather than being movable.

Figure 3:
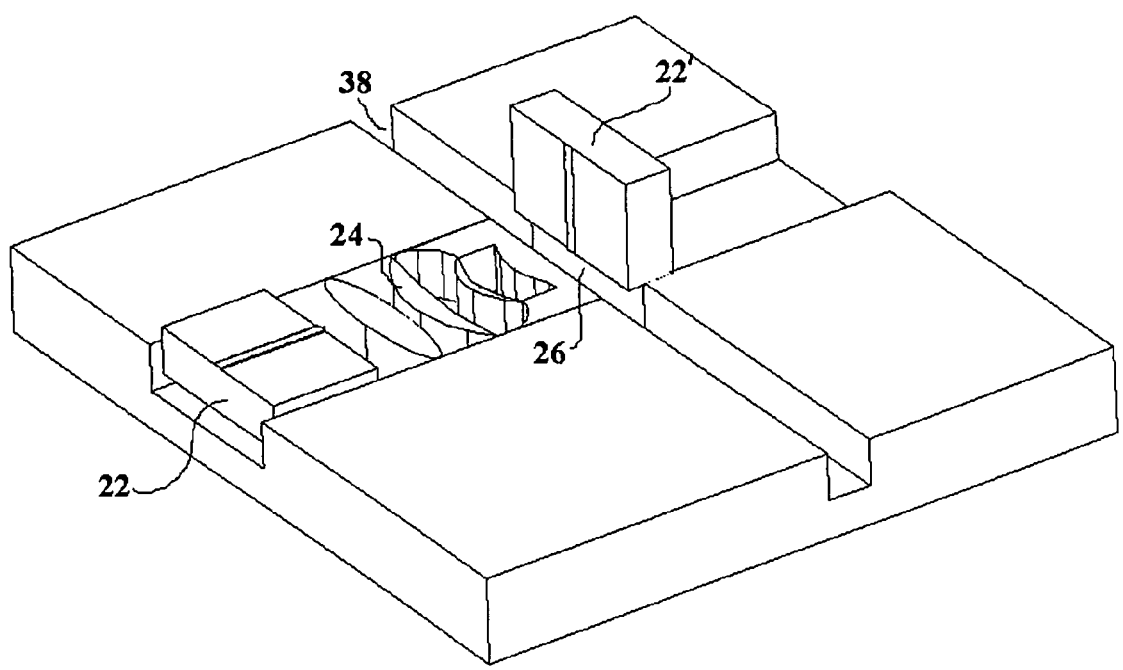
FIG. 3 is a perspective view of a third design including scanning in two directions.

FIG. 3 shows a third embodiment where scanning occurs in two perpendicular directions by placing a second laser diode 22' above the microchannel. In this case, the mirror will be a metal-coated surface of the substrate, and the output signal is detected on the top of the laser diode. Therefore, the biological cells moving through the analysis region are analyzed in both dimensions. The results are finally used to construct a 2D distribution of refractive index inside the cells.

Figure 4A:
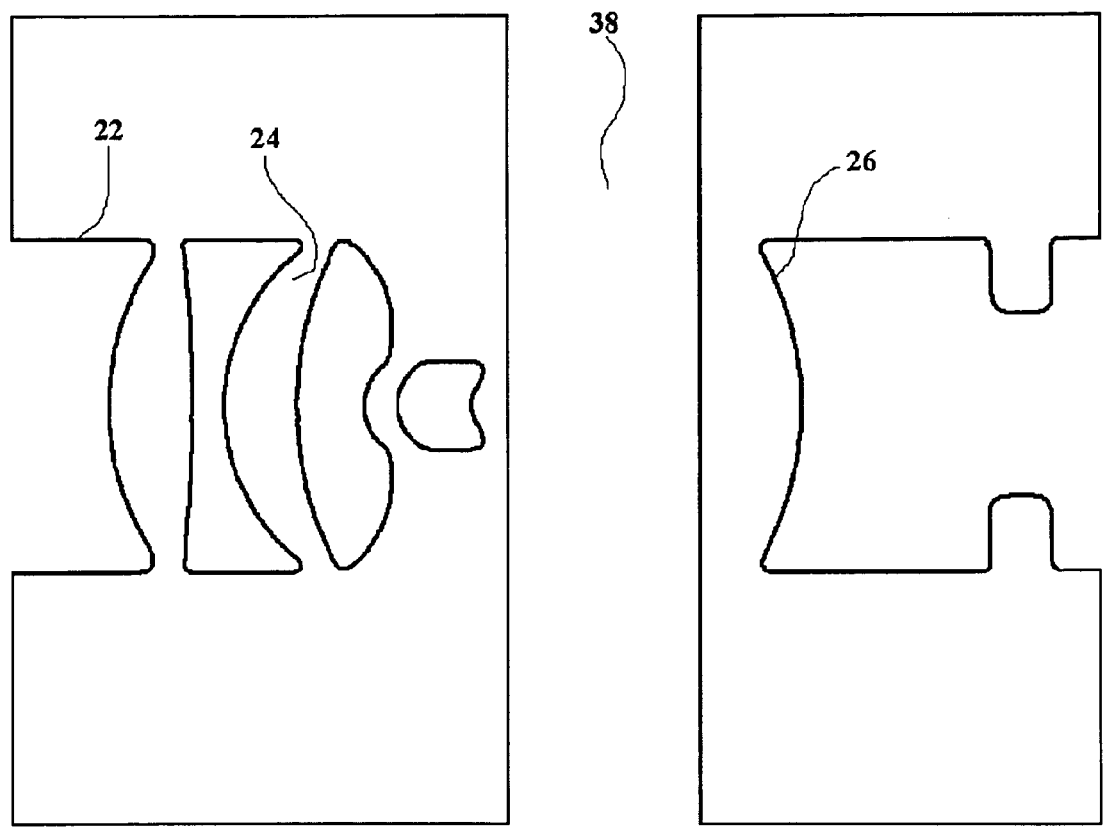
FIG. 4a is a diagram of one design of a microlens set for improving the quality of a laser beam.
Figure 4B:
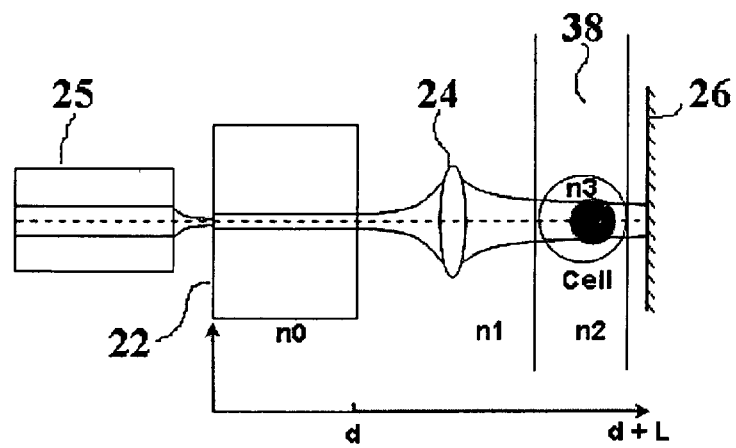
FIG. 4b is a diagram of the optical section of the present invention.

FIG. 4a shows a microlens set and its relationship to the microflow channel. FIG. 4b is a schematic diagram of the optical elements.

In operation, a typical voltage of 100 V/cm from a power supplier is applied to the electrodes at the bottoms of inlet and outlet wells in order to use electrokinetic forces for moving the cells and the solution in which they are placed. The two focusing wells have an relatively higher voltage applied thereto to obtain two high speed streams. The cell flow in the center will be narrowed and the cells will be lined up in the center of the stream. (7) Electrode patterns are coated on the substrate using traditional photolithography material. Thus, the cells move along microchannel 18 to the focusing region. The velocity of the cell flow is set to be about 0.5 mm/s, and the switching is completed within less than 170 ms at this flow speed. Since the EOF flows in the direction of the negative electrode, the target well will have applied thereto a negative pulse when the cell is coming with the other wells being kept open. At the same time, a solution from the focusing wells meets the solution carrying the cells and causes the cells to flow in the center region of channel 38 (7). The cells are also separated so that individual cells can be examined. The cells travel through the analysis unit where light from the laser diode is focused by the microlens set onto the cells. The resultant light is reflected from mirror 26 back into the external cavity. Light from the laser diode is received in optical fiber 25 and carried to an optical detector for a determination of the cell parameters, wherein one end of the optical fiber is put behind the diode and sealed with the substrate, another end of the fiber outside the chip will connect to a photo detector and typically also to a spectrometer through a coupler so that the output power can be analyzed with analysis of the emission spectrum at the same time. Once the cells are identified by the cell parameters after the analysis process, the switch will be set in a corresponding state to steer the cells into separate wells in the sorting region 30.

While FIG. 1 shows a single analysis unit, it is possible for these units to be arranged in parallel for a greater throughput of sample volume. It is also possible to cascade the analysis units so that cells collected in an output well can be reanalyzed to obtain better accuracy or analyzed according to a different parameter for further sorting.

As seen in FIG. 4b, the cells travel through the microfluidic channel 38 to reach the analysis region. When the cell appears within the external cavity of the laser, two phenomena are observed in the parameters of frequency shift and power modulation. Both of these phenomena are functions with respect to a variation in the effective external cavity length.

Based on the theory of laser diodes, the first-order approximation of the emission frequency v and the output intensity I under a weak external feedback are given by (see references 11-14 cited below):

$$v = v_0 - \frac{C\sin[\phi_{ext} + \arctan(\alpha)]}{2\pi\tau_L\{1 + C\cos[\phi_{ext} + \arctan(\alpha)]\}}$$

$$I = I_0[1 + m\cos\phi_{ext}]$$

where $v_0$ and $I_0$ are the laser emission frequency and the intensity without external feedback, respectively. C is an important parameter indicating the external feedback strength, as defined by $$C = \frac{\tau_L}{\tau_d}\xi\sqrt{1+\alpha^2},$$

with $$\xi = \frac{r_3}{r_2}(1 - |r_2|^2)$$

being a constant reflecting the coupling efficiency of the external reflection back into the laser cavity, where $r_2$ and $r_3$ denote the amplitude reflection coefficients of the laser facet and the mirror, respectively. $\tau_d=2n_0d/c$ and $\tau_L=2L/c$ represent the roundtrip time delay inside the laser diode and inside the external cavity, respectively, where $n_0=3.5$ for GaAs is the refractive index (RI) of the laser diode; c indicates the speed of light in vacuum; d and L represent the length of the diode and the effective length of the external cavity depending on the refractive index, respectively. $\alpha$ stands for the linewidth enhancement factor. $\phi_{ext}=4\pi vL/c$ denotes the phase of external reflection. m is the modulation coefficient of the self-mixing interference.

Both the emission frequency and the output power are periodic functions with respect to effective external cavity length L in the presence of the weak feedback. Furthermore, the period of intensity modulation is $\lambda/2$, which means for $\lambda=1.55$ μm, each 0.775 μm change in L will accordingly produce one period of intensity modulation. For this reason, a rough variation of L is obtained by counting the period number of intensity modulation which serves as a rough adjustment mechanism. At the same time, the delicate variation of less than one period is identified by the emission frequency shift that serves for a precision measurement basis. Eventually, the change in external cavity length $\Delta L$ is achieved as the result of combining the rough and delicate segments.

On the other hand, $\Delta L$ can be caused by a change either in the dimension or in the RI of the cavity components based on the expression of L as $$L = \sum_i (n_i \cdot L_i)$$

where $n_i$ and $L_i$ represent the refractive index and the dimension of individual components of the external cavity, respectively. After measuring L and one of the variables on the right side of equation, the remaining one is determined correspondingly. As an example, considering the cases with and without cells in the buffer, the difference of RI between the cell and the buffer results in ΔL described as $$\Delta L = 2r(n_3 - n_2)$$

where $n_3$ and $n_2$ are the RI of cell and buffer, respectively. r is the radius of the cell. Thereby, the RI of the cell is able to be finally calculated after acquiring ΔL.

The theoretical resolution of the system under the weak feedback condition is deduced as $$\Delta L = \frac{\Delta \lambda}{\lambda_0} \cdot \frac{n_0}{\xi \sqrt{1 + \alpha^2}}$$

The resolution of the spectrometer is typically 0.01 nm, the minimum detectable ΔL will be around 10 nm, which corresponds to 0.0005 RI variations for 20 μm cancer cells. The sensitivity and resolution of this measurement system is high enough to distinguish cancerous cells from normal cells since the refractive index difference between the cancerous cells and normal cells is estimated to be approximately 0.02 calculated by the effective medium approximations equation. (15)

Thus, the presence of the cells in the external cavity changes the parameters of the laser itself. Light fed from the laser to fiber 25 can be examined in regard to these parameters so that different cells may be detected by the difference in the parameters of the laser output.

Figure 5A:
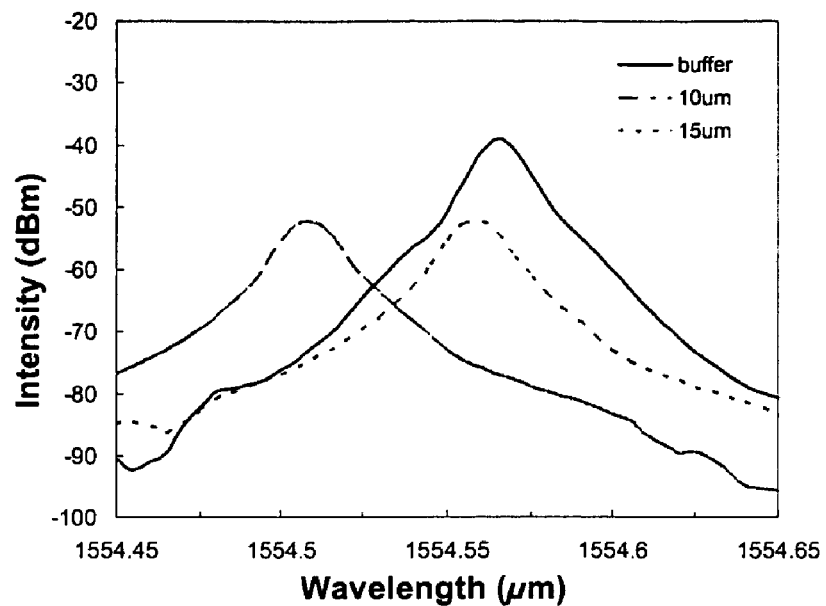
FIGS. 5a and 5b are graphs showing test results for calibration beads.
Figure 5B:
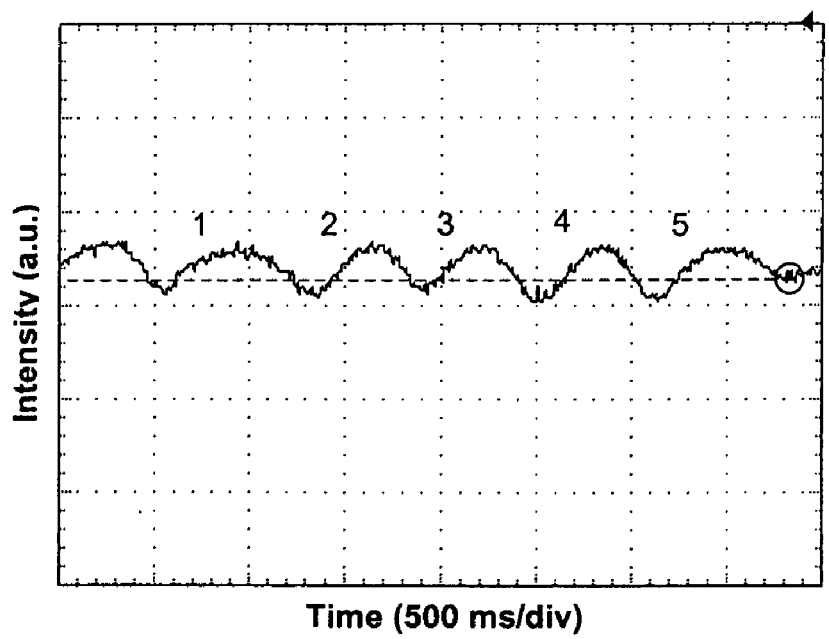

In order to determine the refractive index of cells, the system is calibrated using standard polystyrene beads with a nominal index of 1.59. During the calibration, the emission spectrum and intensity of polystyrene beads are recorded as they pass through the detection region. FIG. 5a shows the wavelength shifts caused by the beads with the diameters of 10 μm and 15 μm, respectively. The emission spectrum shows the wavelength shift is 0.05 nm for 10 μm bead and 0.01 nm for 15 μm, respectively. FIG. 5b shows the effect of the power modulation caused by the bead with a diameter of 15 μm, which produces 5 modulation periods followed by another uncompleted portion that provides the phase information for the precision measurement in the frequency shift. Similarly, the 10 μm bead produces 3 modulation periods. Therefore, the rough changes in L caused by ø10 μm and ø15 μm beads are 3.875 μm (5×λ/2) and 2.325 μm (3×λ/2), respectively.

According to the equation mentioned above, the initial L is calculated to be 436.5 μm, with RI=1.33 in PBS (phosphate-buffered saline) buffer and 403.5 μm in the external cavity length (Refer to the ΔL equation above, 403.5+(1.33−1)× 100=436.5 μm, the width of the channel is 100 μm, the RI of air and PBS are 1 and 1.33, respectively). Inserting the value of wavelength shift and initial cavity length into the equation (1), thus, the refractive indices of ø10 μm and ø15 μm beads are 1.594 and 1.585, respectively. The calibration results are the mean values of three measurements with a marginal difference of 0.25%, which rigorously match the nominal value 1.59. (11)

Once the system is calibrated, living cells may then be measured. FIGS. 6a-6e show different types of cancerous cells which can be measured with this technique. These cells have refractive indices which are subsequently determined after the cell sizes are measured through those microscopy images (6). The photos are taken under an inverted microscope when the cells pass through the analysis region. FIG. 6a shows a HeLa cell, a cell derived from cervical cancer cells; FIG. 6b is PC12 cell, a clonal cell line derived from a transplantable rat adrenal pheochromocytoma; FIG. 6c MDA-MB-231, a human cell line which is a prototype for study of hormone-independent breast cancer; FIG. 6d MCF-7, a type of breast cancel cells; FIG. 6e Jurkat cell, a CD4 T-cell leukemia cell.

All cells are cultivated in the culture medium of DMEM (Dulbecco's modified Eagle's medium) containing 10% FBS (fetal bovine serum), and the concentration of cells is diluted to around ten cells per microliter with PBS buffer for the experimental measurement. The external cavity length L for cell measurement is fixed to 250 μm when the buffer is free of cells. Cell size is determined by microscopy imaging technology such as shown in FIGS. 6a-6e. (6) At the end of the experiment, the effective refractive index of the cells is calculated; they are 1.392, 1.395, 1.399, 1.401, and 1.390 respectively. All indices of cancerous cells tested are larger than 1.37, which is the typical RI of normal cells (16). Thus, the changes to cells that provide a cancerous phenotype result in a relatively larger effective refractive index even though the whole size of the cells remains consistent. The results of experiments imply that an increase in RI of the living cells is a marker for cells turning malignant, which enables a diagnosis of cancers in the early development of the diseases without any requirement of sample treatment.

Thus, the present system and method can be used to measure the refractive index of a single living cell so that any disease which produces a change in refractive index can be screened for by use of this technique. This includes many of the various cancer diseases. Further, cell size can be analyzed by the same apparatus when the refractive index of the cell is determined before the measurement. If the laser light is narrowed down to 1-3 μm by the microlens set, the cell size is continuously scanned and calculated in two dimensions as the cell is moving through the analysis region, hence, the shape of the biological cell can be reconstructed according to the recorded data. The laser beams serve as the scanners like the tip in atom force microscope (AFM), after scanning, the shape profile is regenerated.

Thus, by scanning the cells in an external cavity, the light emitted from the laser can detect very small differences in effective cavity length which allows a determination of different types of cells so that they may be sorted and classified. The result of this is a very accurate and simple device which is inexpensive to produce.

REFERENCES CITED

The following references are hereby incorporated by reference in their entirety and for all purposes:
1. M. Valcarcel and S. Cardenas, *Trands in Analytical Chemistry*, 21, 211, (2002).
2. T. Katsuragi and Y. Tani, Journal of Bioscience and Bioengineering, 89, 217, (2000).
3. H. S. Sorensen, H. Pranov, N. B. Larson et al. *Analytical Chemistry*, 75, 1946, (2003).
4. J. J. Lunazzi and M. Garavaglia, *Journal of Physics E: Scientific Instruments*, 6, 237, (1973).
5. P. L. Gourley and M. F. Gourley, U.S. Pat. No. 5,608,519, 1997.
6. Y. D. Tchoukalova, D. A. Harteneck et al. *Journal of Lipid Research*, 44, 1795, (2003).
7. Y. Sun, L. C. Ng, A. Q. Liu et al. *Proceeding of Asia-Pacific Conference of Transducers and Micro-Nano Technology* 2004, 267-271, Sapporo, Japan, Jul. 4-8, 2004.

8. R. Barer, *Journal of the Optical Society of America*, 47, 545, (1957).
9. X. J. Liang, X. M. Zhang, A. Q. Liu et al. *Proceeding of Asia-Pacific Conference of Transducers and Micro-Nano Technology* 2004, 276-280, Sapporo, Japan, Jul. 4-8, 2004.
10. J. C. Mcdonald and G. M. Whitesides, *Accounts of Chemical Research*, 35, 491, (2002).
11. K. Petermann, *Laser Diode Modulation and Noise* (Kluwer Academic Publishers, Netherlands, 1998).
12. A. Q. Liu, X. M. Zhang, V. M. Murukeshan, C. Lu, and T. H. Cheng, *IEEE Journal on Selected Topics in Quantum Electronics*, 8, 73, (2002).
13. X. M. Zhang, A. Q. Liu, D. Y. Tang, and C. Lu, *Appli. Phys. Lett*, 84, 329 (2004).
14. A. Q. Liu, X. M. Zhang, D. Y. Tang, and C. Lu, *Appli. Phys. Lett*, 85, 3684 (2004).
15. M. I. Mishchenko, J. W. Hovenier, and L. D. Travis, *Light Scattering by Nonspherical Particles: Theory, Measurements, and Applications* (Academic Press, UK, 2000).
16. J. B. Hahn, C. H. Fox and B. Thorell, *Journal of Cell Biology*, 82, 767, (1979).
17. V. Backman, M. B. Wallace et al. *Nature*, 406, 35, (2000).
18. C. C. Chen, Y. L. Tsai, C. L. Hsu, and J. Y. Chang, *Optics Express*, 12, 3934, (2004).
19. T. Nakai, T. Kannamori, S. Sando, and Y. Aoyama, *J. Am. Chem. Soc*, 125, 8465, (2003).
20. A. Ehrlicher, T. Betz, B. Stuhrmann et al. *Proc. Nat. Aca. Sci. USA*, 99, 16024, (2002).
21. A. T. C. Lee, H. L. P. Azimahtol and A. N. Tan, *Cancer Cell International*, 3, 16, (2003)

What is claimed is:

1. An integrated apparatus for analyzing biophysical parameters of cells, comprising:
a substrate;
a microfluidic structure mounted on said substrate;
a cell analysis unit integrated with said microfluidic structure, including a laser light source and an external laser cavity; and
an electrical circuit including a plurality of electrodes;
wherein the external laser cavity includes a microchannel of said microfluidic structure, and one surface of said laser light source and a mirror parallel to said surface are disposed opposite each other across said microchannel, and a microlens set that focuses the beam from said laser light source through a focusing region in said microchannel, and focuses laser light reflecting from said mirror back to said laser light source so as to influence the output of said laser light source.

2. The apparatus of claim 1, wherein the laser light source is a laser diode.

3. The apparatus of claim 2, wherein the laser diode is one of a natural cut surface with a reflectance of about 30% and one surface anti-reflective coated with a reflectance of about 0.1%.

4. The apparatus of claim 1, wherein said mirror is coated with gold.

5. The apparatus of claim 4, where the mirror is a plane mirror to form a Fabry-Perot cavity.

6. The apparatus of claim 4, where the mirror is a curved mirror to form a plane-concave or plane-convex cavity.

7. The apparatus of claim 4, where the mirror is metal-coated aperture face of an optical fiber.

8. The apparatus of claim 1, where the mirror is adjustable by a micromachining actuator.

9. The apparatus of claim 1, wherein the microlens is a planar microlens.

10. The apparatus of claim 9, wherein the planar microlens is fabricated with the microfluidic system and improves beam quality.

11. The device of claim 1, where the substrate is a hard material.

12. The apparatus of claim 1, wherein the said electrical circuit applies an electric field to manipulate a microflow through said microfluidic structure.

13. The apparatus of claim 1, wherein said electrodes are located on wells and generate an electrokinetic force for manipulating and driving said cells.

14. The apparatus of claim 1, wherein said electrodes are coated on the substrate, beneath a main channel of said microfluidic structure and on the side opposite the microfluidic structure.

15. The apparatus of claim 1, wherein the microfluidic system contains a focusing structure to narrow the width of cell flow by squeezing a cell stream from both sides with a focusing buffer.

16. The apparatus of claim 15, wherein a switching structure sorts said cells to output wells after being analyzed.

17. A method of sorting biological cells, comprising the steps of:
injecting a cell sample comprising cells to be analyzed into an inlet;
applying an electric field to said inlet, focusing reservoirs and outlets to drive and steer a cell flow in which cells are separated one from another;
placing one cell to be analyzed in a cell analysis region, said region being formed as an external cavity of a laser light source that includes a microchannel, and one surface of said laser light source and a mirror parallel to said surface are disposed opposite each other across said microchannel,
said cell analysis region further comprising a microlens set that focuses the beam from said laser light source through focusing region in said microchannel, and focuses laser light reflecting from said mirror back to said laser light source so as to influence the output of said laser light source;
encoding an emission from said laser based on parameters of said cell to be analyzed; and
sorting said cell into an appointed well based upon a signal of said encoding.

18. The method according to claim 17, where said cell sample is injected by pipette.

19. The method according to claim 17, wherein different velocities of flow are obtained using electrical fields of different value or polarity.

20. The method according of claim 17, wherein said cells are focused to a single cell width so that cells move through said analysis region one at a time.

21. The method according to claim 17, wherein the cells are detected by measuring an optical characteristic of the laser emission.

22. The method according to claim 17, wherein the cell analysis region comprises two laser light sources for scanning in different directions.

23. A method of analyzing a biological cell, comprising the steps of:
providing a cell analysis region as an external cavity of a laser light source that includes a microchannel, and one surface of said laser light source and a mirror parallel to said surface are disposed opposite each other across said microchannel,
said cell analysis region further comprising a microlens set that focuses the beam from said laser light source through focusing region in said microchannel, and focuses laser light reflecting from said mirror back to said laser light source so as to influence the output of said laser light source;

placing the cell to be analyzed in the cell analysis region;

varying an external feedback strength of said external cavity based on a parameter of said cell so as to vary an emission of the laser; and analyzing light emitted from said laser to determine a value of said parameter.

24. The method according to claim 23, wherein the parameter is the refractive index of the cell.

25. The method according to claim 23, wherein the laser emission is varied in frequency.

26. The method according to claim 23, wherein the laser emission is varied in intensity.

27. A cell analysis unit for analyzing biophysical parameters of cells, comprising:

a microchannel; a laser light source wherein one surface of said laser light source and a mirror parallel to said surface are disposed opposite each other across said microchannel;

a microlens set that focuses the beam from said laser light source through a focusing region in said microchannel, and focuses laser light reflecting from said mirror back to said laser light source so as to influence the output of said laser light source.

28. The unit of claim 27, wherein the laser light source is a laser diode with one of a natural cut surface with the reflectance of about 30% and one surface anti-reflective coated with the reflectance of about 0.1%.

29. The unit of claim 27, wherein the mirror is adjustable by a micromachining actuator.

30. The unit of claim 27, wherein the external cavity further includes a planar micro lens set between said mirror and said surface.

* * * * *